(12) United States Patent
Barghelame

(10) Patent No.: US 7,108,712 B2
(45) Date of Patent: Sep. 19, 2006

(54) SAUNA WITH PHOTOTHERAPY LIGHTING

(76) Inventor: Si Barghelame, 18514 NE. 143rd Pl., Woodinvillle, WA (US) 98072

( * ) Notice: Subject to any disclaimer, the term of this patent is extended or adjusted under 35 U.S.C. 154(b) by 322 days.

(21) Appl. No.: 10/624,339

(22) Filed: Jul. 21, 2003

(65) Prior Publication Data
US 2004/0030371 A1 Feb. 12, 2004

Related U.S. Application Data

(63) Continuation of application No. 09/684,685, filed on Oct. 7, 2000, now abandoned.

(60) Provisional application No. 60/158,593, filed on Oct. 7, 1999.

(51) Int. Cl.
A61N 5/06 (2006.01)

(52) U.S. Cl. ............................................ 607/91; 607/88

(58) Field of Classification Search ................... 607/80, 607/81, 100; 4/524–526
See application file for complete search history.

(56) References Cited

U.S. PATENT DOCUMENTS

| | | | | |
|---|---|---|---|---|
| 4,114,205 A | * | 9/1978 | Muller | 607/80 |
| 4,277,855 A | * | 7/1981 | Poss | 4/524 |
| 4,446,356 A | * | 5/1984 | Rimmi | 392/386 |
| 4,773,105 A | * | 9/1988 | Toyoshima | 4/526 |
| 5,117,481 A | * | 5/1992 | Sung | 392/416 |
| 5,227,693 A | * | 7/1993 | Sakakibara et al. | 313/489 |
| 5,255,399 A | * | 10/1993 | Park | 4/525 |
| 5,811,924 A | * | 9/1998 | Okumura et al. | 313/487 |
| 6,055,684 A | * | 5/2000 | Azuma | 4/526 |

OTHER PUBLICATIONS

Data sheets for Chromalux lights, Atlanta Light Bulbs, Atlanta, Ga. and Truesun.com.*

Data Sheet for Verilux Natural Lighting Lamps.*

* cited by examiner

Primary Examiner—Roy D. Gibson
(74) Attorney, Agent, or Firm—Garrison & Associates PS; David L. Garrison

(57) ABSTRACT

A radiant, infrared heat sauna with full spectrum, Neodymium or similar lighting. The sauna is portable and can be plugged in to run on standard household current. Radiant heating elements in the walls of the sauna emit infrared rays directly into a person's body, creating penetrating heat thus producing sweat and an overall warming sensation, as well as the provided overhead, adjustable full spectrum lighting which creates a sensation of sunlight on the body. At least one embodiment of the invention includes full spectrum lighting on the walls of the sauna. Embodiments of the invention can also include sound systems, video systems, and aromatherapy devices. The combination of the infrared heating and the full spectrum lighting comes close to recreating the feeling of warmth and well being of enjoying time in the sun, without the harmful UV rays.

16 Claims, 6 Drawing Sheets

SAUNA WITH PHOTOTHERAPY LIGHTING

CROSS REFERENCE TO RELATED APPLICATION

This application is a continuation of U.S. Utility patent application Ser. No. 09/684,685, entitled "Sauna with Phototherapy Lighting, filed Oct. 7, 2000 now abandoned, which claims benefit of Provisional Patent Application No. 60/158,593, filed Oct. 7, 1999, entitled "SUN BOX SAUNA AND LIGHT FIXTURE".

FIELD OF INVENTION

The current invention relates to the field of phototherapy lighting and saunas. Specifically, the current invention discloses phototherapy lighting located within a portable sauna, where such sauna and phototherapy lighting combination provides a therapeutic and aesthetic experience that approximates the rays of natural sunlight.

BACKGROUND OF THE INVENTION

Saunas have been manufactured and sold on the market for many years. Saunas can employ a variety of heat sources, all with the object of warming a person's body in order to create sweat. The sweating process has several health benefits such as increasing the heart rate, blood circulation, calorie consumption, and the release of toxins.

Phototherapy, or light therapy, is a newer science that has developed in particular in respects to the treatment of Seasonal Affected Disorder (SAD). Phototherapy was found to be highly effective in the treatment for SAD, or seasonal affective disorder, as well as effective for re-tuning the biological time clock, alleviating stress and creating endorphins for mood enhancement. In addition, more recent research has indicated that light therapy addressed to the body as a whole in conjunction with heat therapy to the body increases the beneficial aspects of both.

Until this point, no one has yet addressed the need or found a way to provide full body phototherapy and heat therapy in a comfortable, pleasant and affordable manner. This invention is in response to that current need.

A search of sauna patents yield none that are concerned with phototherapy. U.S. Pat. No. 4,846,145 to Katsuyoshi (1989) concerns itself with the combination of combustion heat and infrared heat to a sauna. U.S. Pat. No. 5,628,073 to Popovich (1997) relates to a portable sauna of tubular metal and a thermal shield.

A search of phototherapy patents is a little more helpful. U.S. Pat. No. 5,562,719 to Lopex-Claros (1996) indicates a method of delivering phototherapy to the eyes via a mask. U.S. Pat. No. 5,447,527 to Waldman (1995) indicates a method of delivering phototherapy to the eyes via a table lamp apparatus.

No patents indicate phototherapy to the entire body as well as the eyes. Recent research indicates that the beneficial light therapy as also absorbed by the skin. U.S. Pat. No. 5,645,578 by Sybaritic, Inc. (1997) makes some attempt to combine heat and phototherapy. The phototherapy is concerned however, only with the person's eyes. The person's head is covered with a stationary hood which is in turn attached with the bed frame. The bed frame is encased in a covering that delivers heat. The user will not receive the benefits of full body light therapy. In addition the user will be forced to lie still in a bed, with his head encased in a hood while flashing lights pass in front of his eyes. The hood and bed apparatus limit the user's mobility, makes him unaware and not in control of his surroundings, deprives him of full body light therapy and makes him unable to do other activities such as reading. This type of therapy could be claustrophobic and limiting to the extent that the user would not be very eager to employ it.

SUMMARY OF THE INVENTION

It is an object of this invention to provide the benefits of phototherapy to the entire body and the eyes.

It is also an object of this invention to create a more enjoyable experience for the use of light therapy.

Another object of this invention is to create a more enjoyable experience for the use of a sauna by alleviating the sometimes dark, cave-like atmosphere.

Yet another object of this invention is to provide a sauna that can help improve one's mood and alleviate the symptoms of Seasonal Affected Disorder (SAD).

A further object of this invention is to provide a sauna that can help reset one's biological clock in cases of jet lag.

It is also an object of this invention to provide a sauna that can be used for a combination of heat and light therapy for the entire body having enhanced therapeutic properties over existing technologies.

A yet further object of this invention is to provide an affordable mechanism to be used at home or in institutions.

The sauna of the current invention is an constructed of natural, untreated, cedar or similar wood, with a seating bench placed at a comfortable height from the floor. The overall size of the enclosure can vary from one person to several. The front of the enclosure has an entry door, hinged on one side, with a magnetic door closure on the other side, that does not allow locking. The door contains a window and the front of the sauna also displays a circular window as a part of its signature appearance.

For simplicity and quickness of assembly and storage, the two side panels are hinged to the back panel and can be folded flat. The floor, bench, the light box (describe below) and front panel are separate and attach easily with minimal tools through special clasp or clamp closures already pre-attached to the pieces. The side and back wall contain preassembled slots to slide the bench into.

The base is notched around the exterior edges for the sides, front and to fit into before being clamped down, for added stability of the unit. The top of the enclosure is comprised of a box containing a plurality of full spectrum lights that rests on the sidewalls and the back wall. The enclosure can include air vents and in one embodiment of the invention there is an air vent under the bench and another air vent near the top of the enclosure.

Preferred embodiments of the invention contain infrared heating units, full spectrum lighting and audio systems. The electronic components of the invention are powered by standard household current and the saunas of the current invention can simply be plugged into a standard wall socket.

The infrared radiant heaters are positioned strategically in the walls of the enclosure to provide evenly distributed infrared heating rays onto a person sitting inside the enclosure. The light box contains a plurality of full spectrum incandescent or florescent neodymium or similar light sources. The light box is specially designed to direct rays in a parallel formation, thus providing a light source similar to the characteristics of the sun's light, without the harmful UV rays. At least one preferred embodiment of the invention can also include the full spectrum lights placed on the walls in addition to the light box, so that a user of the sauna is surrounded in a light bath.

The sheltered area beneath the bench is cooler and suitable for placement of a sound system or speakers. In some embodiments of the current invention, aromatherapy devices may be enclosed in area beneath the bench or on one of the interior walls of the unit.

A control panel for the heating elements, the sound system, and the intensity of the lights, as well as for the corresponding times, is conveniently located both outside and inside the unit. The infrared heating elements are thermostatically controlled to provide a predetermined comfortable range of heating intensity. The thermostatic controls can be set manually for a comfortable temperature.

At least one embodiment of the current invention includes a built in timer as well that can be set and will turn off the heat after the desired time. The neodymium light box is controlled by a variable resistance dimmer switch specially designed to increase intensity of the lights from low to high automatically in a gradual manner over a period of approximately 5–10 minutes or longer thus duplicating the sensation of a sunrise. The light controls also have a timer that can be set to turn off the lights either gradually or instantaneously at a desired time.

The current invention meets the objects stated above by providing a portable sauna having infrared heat and full spectrum light capabilities. The enhanced combination further saves time for the users as light and heat therapy can be used together; saves space as only one unit is required and thus saves on cost as well. The user can experience the benefits of light and heat therapy while engaging in other activities such as reading, listening to music, or even watching pictures or entertainment on a mounted screen. For total relaxation the user can bask in the warmth and light that resembles being outside on a sunny day.

BRIEF DESCRIPTION OF THE SEVERAL VIEWS OF THE DRAWINGS

FIG. 12 is a view, seen from below, of a light receptacle having rings of mirrors for directing light rays, as.

DETAILED DESCRIPTION

Figure 1:
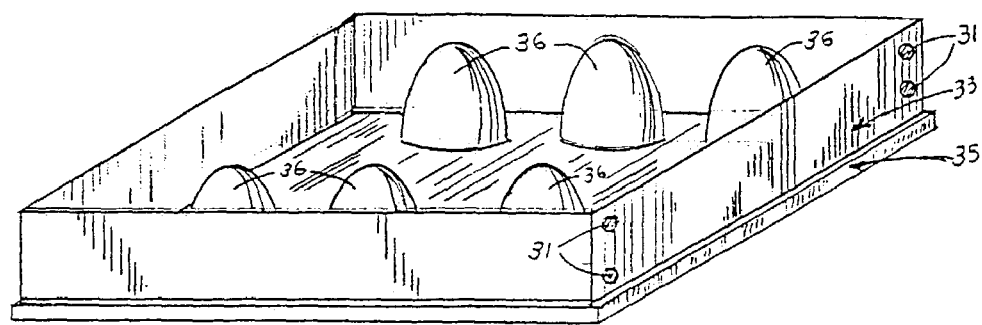
FIG. 1 shows a box containing the phototherapy unit that comprises the top of the sauna.
Figure 6:
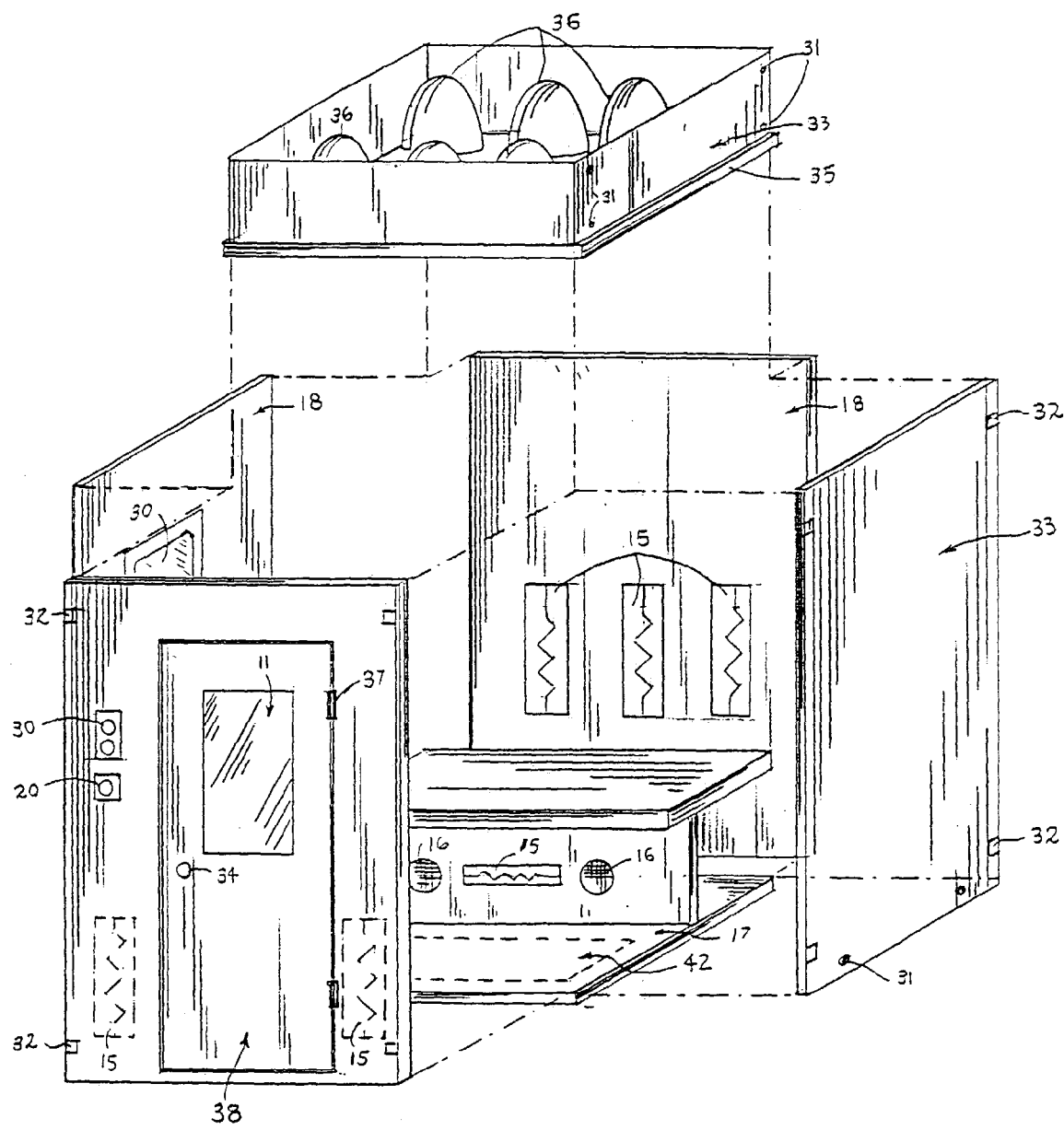
FIG. 6 shows an exploded view of the sauna, exhibiting some of the outside and interior features.

Turning now to the drawings, the invention will be described in preferred embodiments by reference to the numerals of the drawing figures wherein like numbers indicate like parts. One preferred embodiment of this invention is illustrated in FIG. 1 and FIG. 6, the exterior surface 33 and the interior surface 18 of the sauna are constructed of wood, preferable cedar. The door 38 contains a window 11 and connection hinges 37 and a door handle 34 with a magnetic closure.

Figure 2:
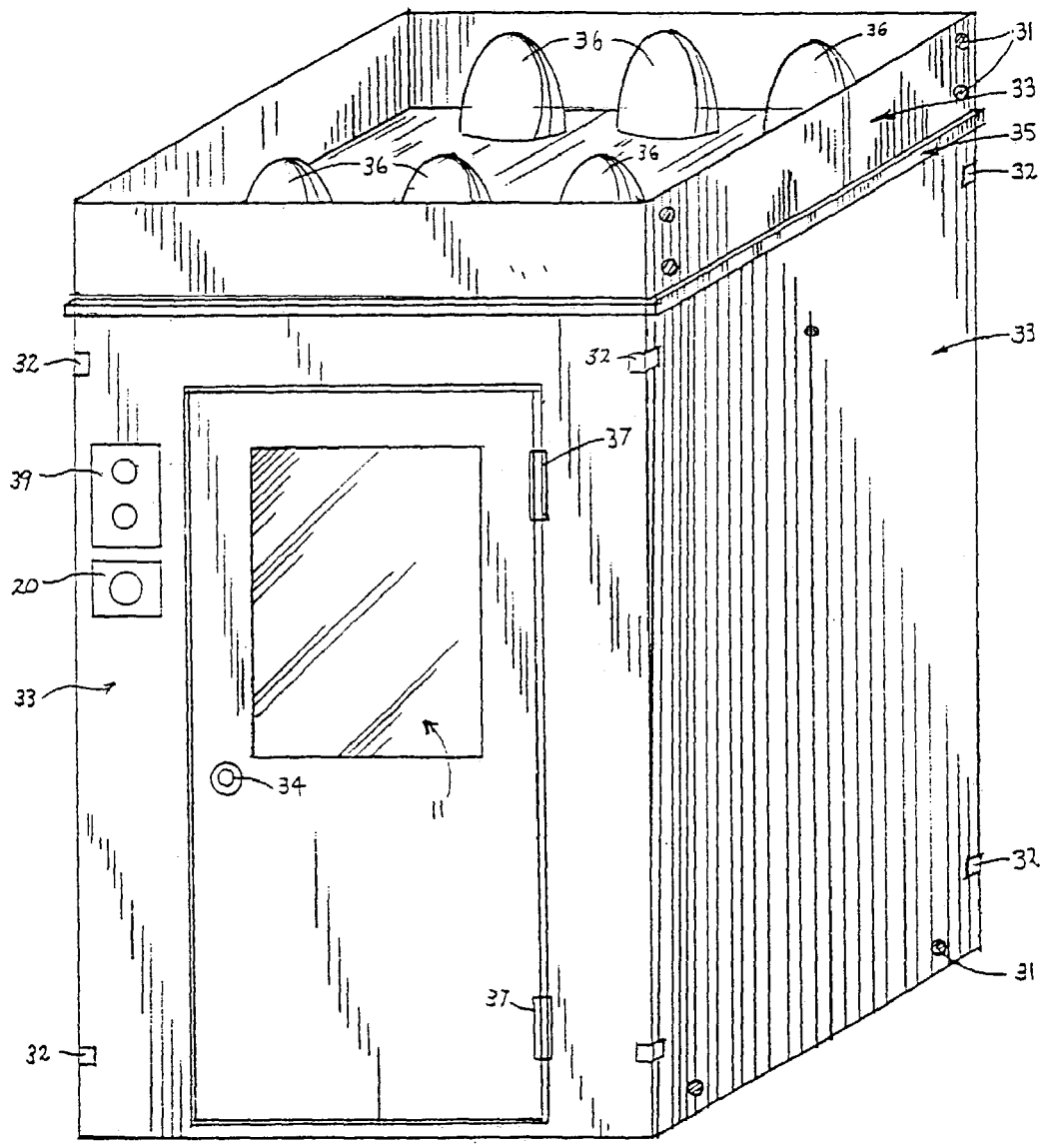
FIG. 2 shows the exterior view of the sauna from the front and side.

The sides of the sauna are connected by pre-attached clamps 32 and screw assemblies 31. The top of the sauna, consisting of the phototherapy light box contains a wood strip 35 at its base, which overlaps the top of the unit and is held on by gravity. The interior bench 27 is held up by its connection to the back wall and the vertical panel 26. FIG. 2 and FIG. 6 also show the exterior placement for the control panel 39.

Figure 3:
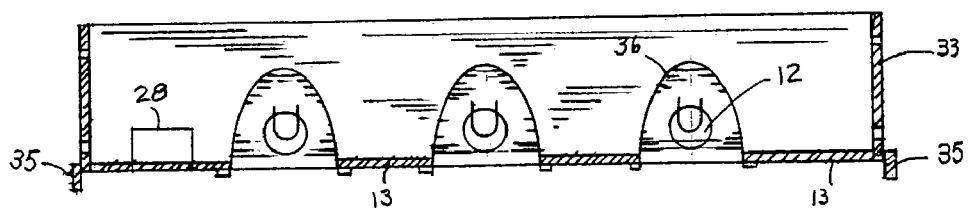
FIG. 3 shows a cross section of the phototherapy light box.
Figure 4:
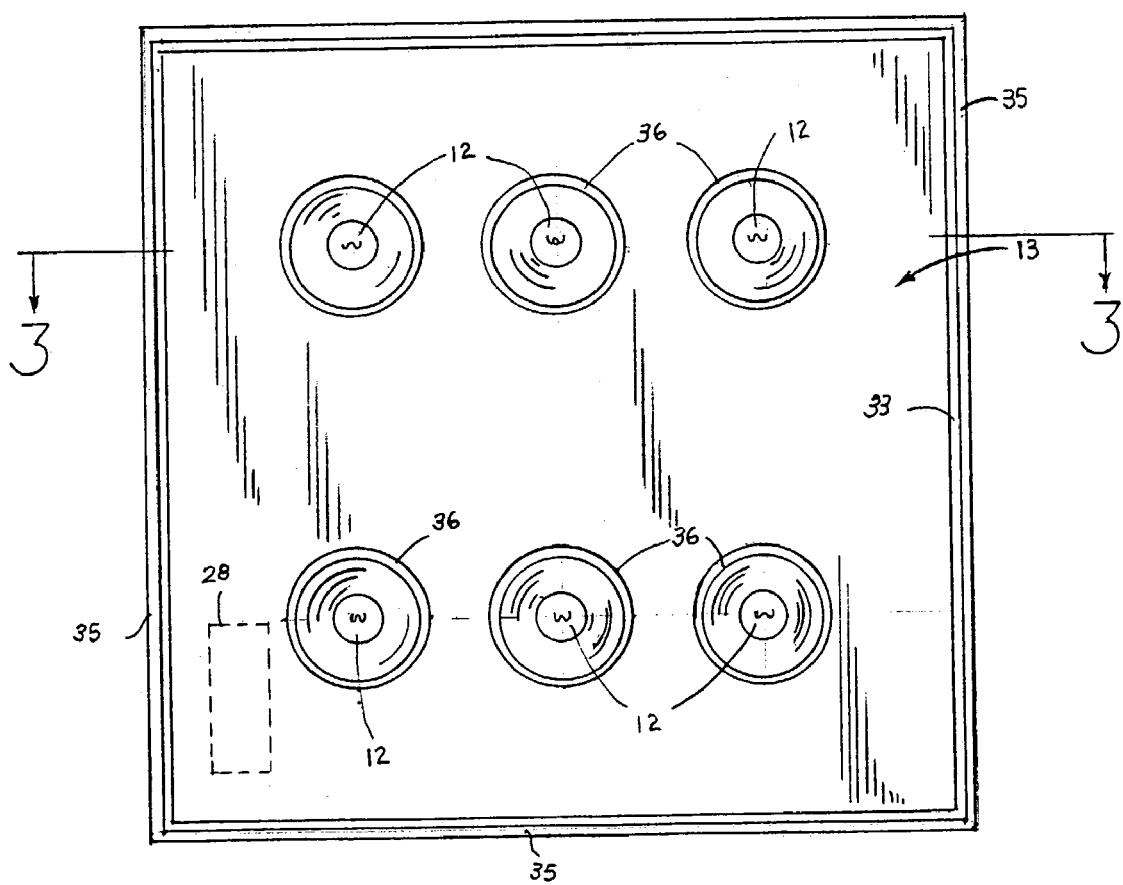
FIG. 4 shows the ceiling view of the phototherapy light box from inside the sauna
Figure 5:
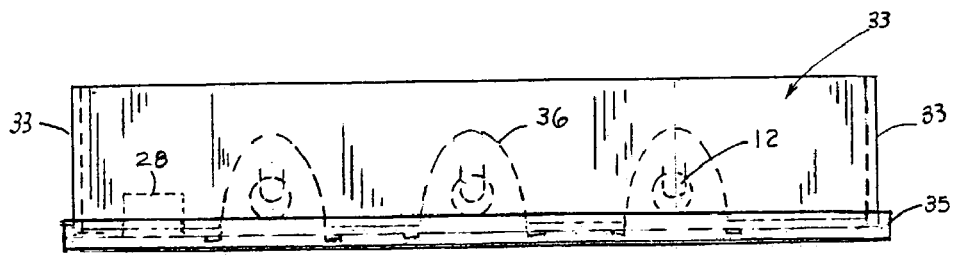
FIG. 5 shows the front view of the phototherapy light box.

FIGS. 3, 4, and 5 show the physical structure of the phototherapy light box, which fastens to the top of the sauna unit. It is comprised sides 33, a vented top, and a lower panel 13 with a plurality of circular holes to direct light into the sauna. Each hole contains a light element 12. The entire box is built slightly larger that the dimensions of the sauna, so that the overhanging lip 35 of the box fits over and attaches to the top of the sauna.

The recessed light canister assembly 36 is shown from the side and the top. The full spectrum light bulb 12 is shown located inside of the housing. The interior ceiling surface of the phototherapy light box 13 is constructed of wood, preferably cedar to match the rest of the interior of the sauna. An inlet power box and relay housing 28 is located behind the ceiling surface 13. The panel of the light box contains ventilation holes to allow adequate heat dissipation.

Figure 7:
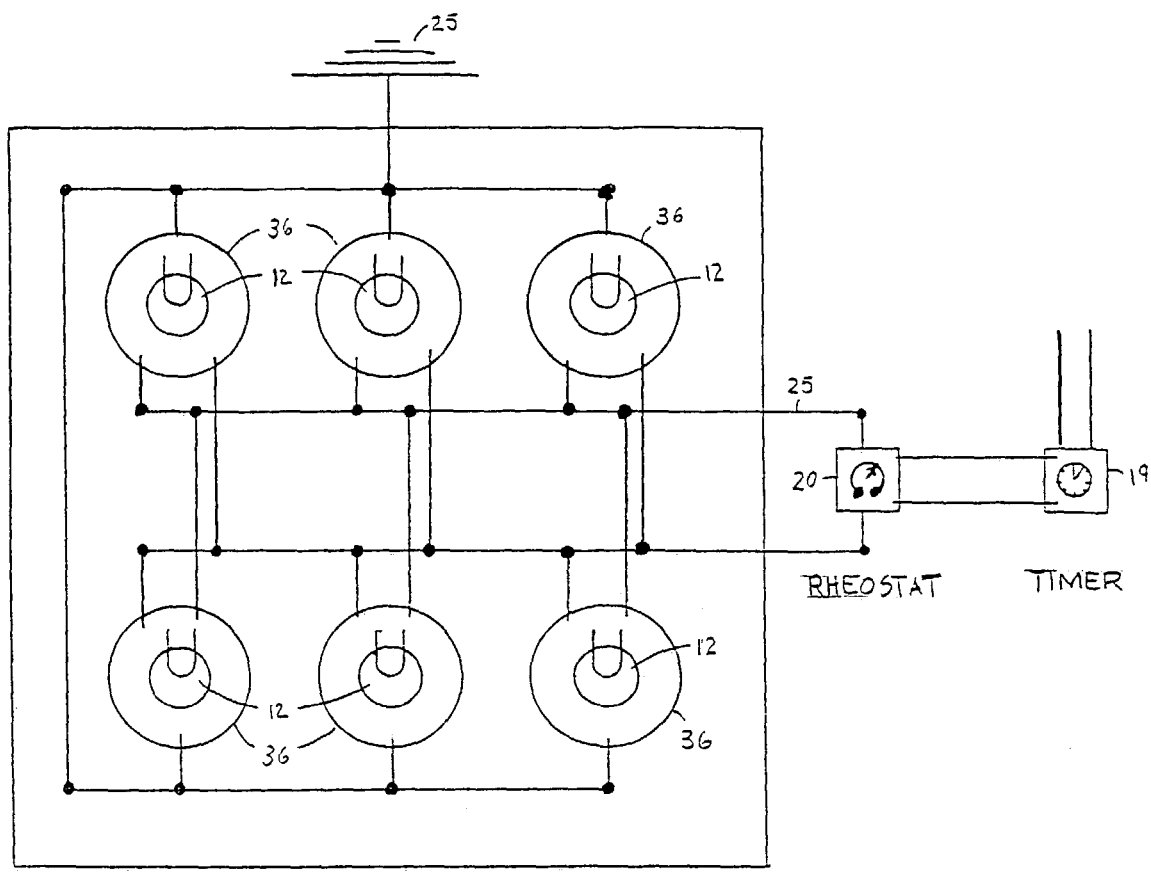
FIG. 7 shows the wiring diagram for the phototherapy light box.

FIG. 7 shows the wiring 25 of the light bulbs 12 to the grounding rod 21, the rheostat 20, and the timer switch 19. The number of bulbs will vary base on the overall size of the sauna. While not depicted, the timer can be used in conjunction with variable resistance dimmer to increase intensity of the lighting in a slow and gradual manner to recreate a feeling of a sunrise and allow a comforting adjustment of the eyes to the light. Manual settings of intensity are also possible. In addition the timer can be set to gradually diminish and turn off the lights or turn them off all at once, at a predetermined time.

Figure 8:
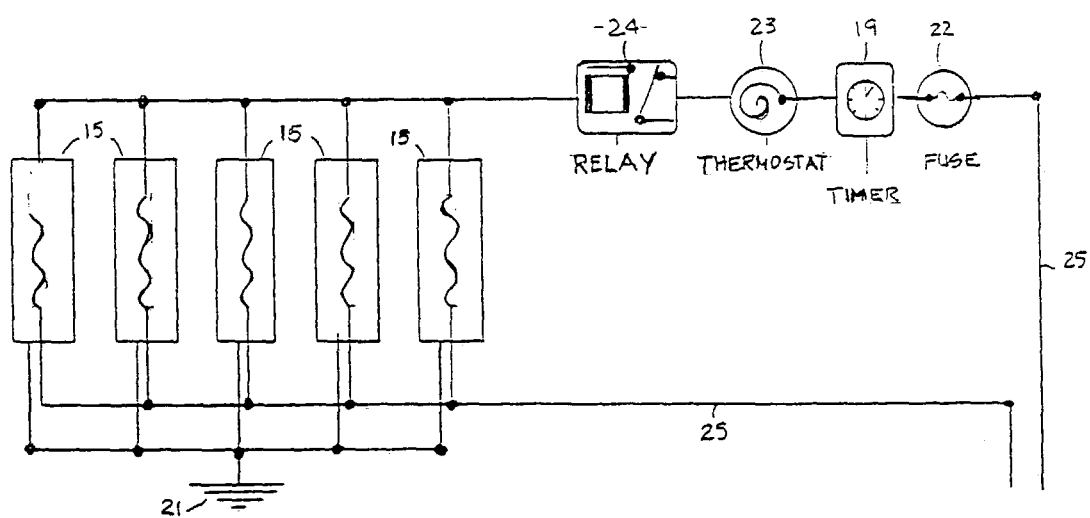
FIG. 8 shows the wiring diagram for the heating elements.

FIG. 6 shows the manner in which the sauna can be disassembled. In addition, the placement of the heating units 15 as well as the speakers 16 is shown. FIG. 8 shows the wiring 25 of the heating units to the grounding rod 21, the relay 24, the thermostat control 23, the timer switch 19, and the fuse 22.

Figure 9:
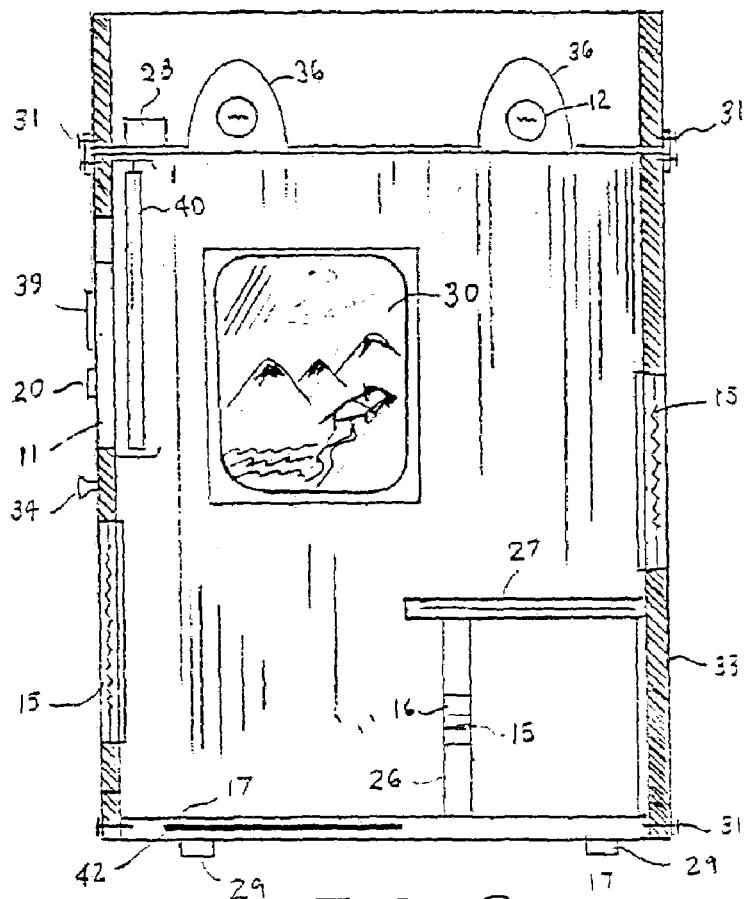
FIG. 9 shows cross section displaying interior sidewall of the sauna.
Figure 10:
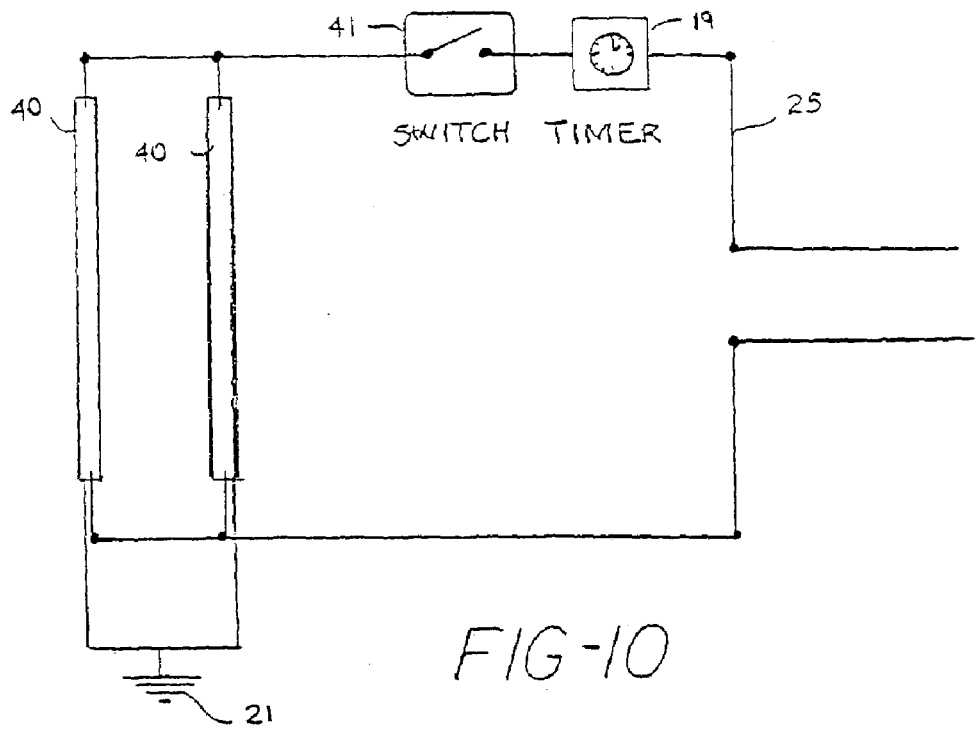
FIG. 10 shows the wiring diagram for the ultraviolet lighting.

FIG. 9 shows an embodiment of a sauna according to the current invention that has a screen for moving pictures 30, magnets 42 in the floor and a UV bulb 40 mounted on the wall. A footing block 29 is displayed beneath the sauna. While not depicted in the figures, at least one embodiment of the current invention has full spectrum neodymium or similar lights in the walls of the sauna to provide a user with a total light bath. FIG. 10 shows the wiring 25 connecting the ultraviolet lights 40 to the switch 41 and the timer 19.

Figure 11:
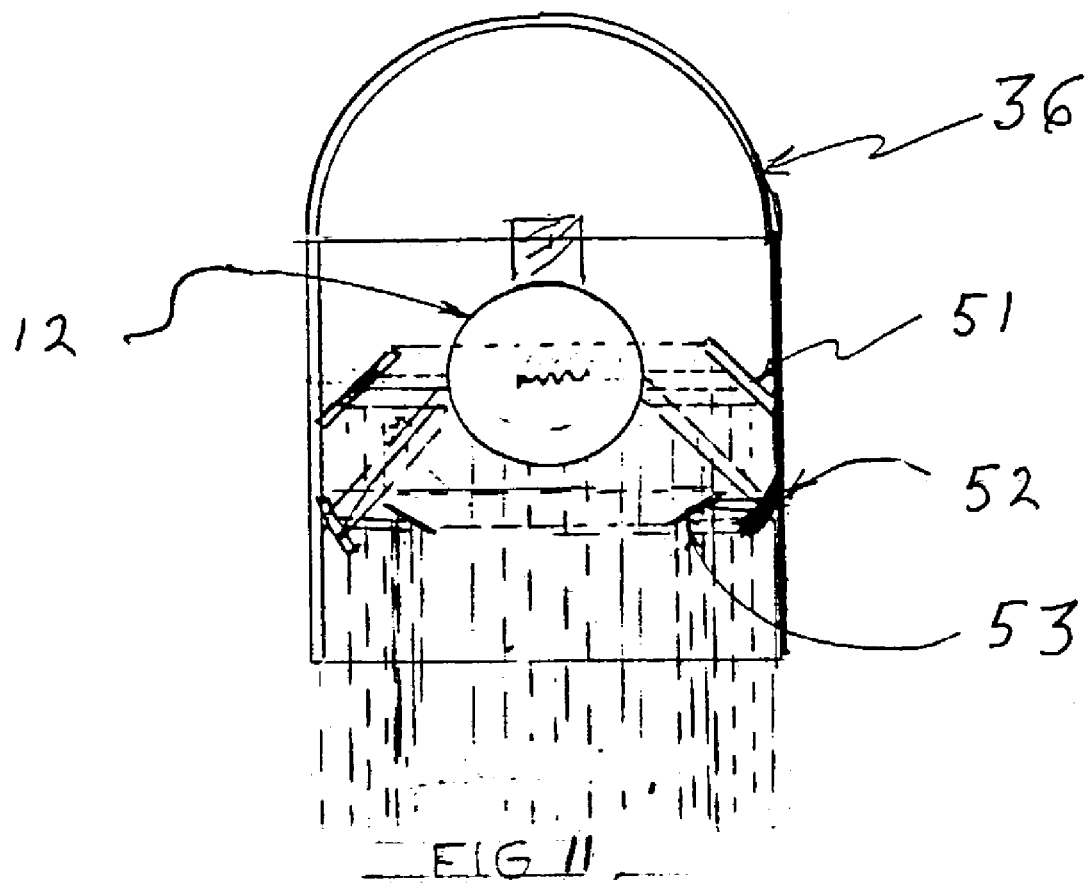
FIG. 11 is a cross sectional side view of a light receptacle in the light box, illustrating the use of mirrors for directing the rays of full spectrum lights from the light box.
Figure 12:
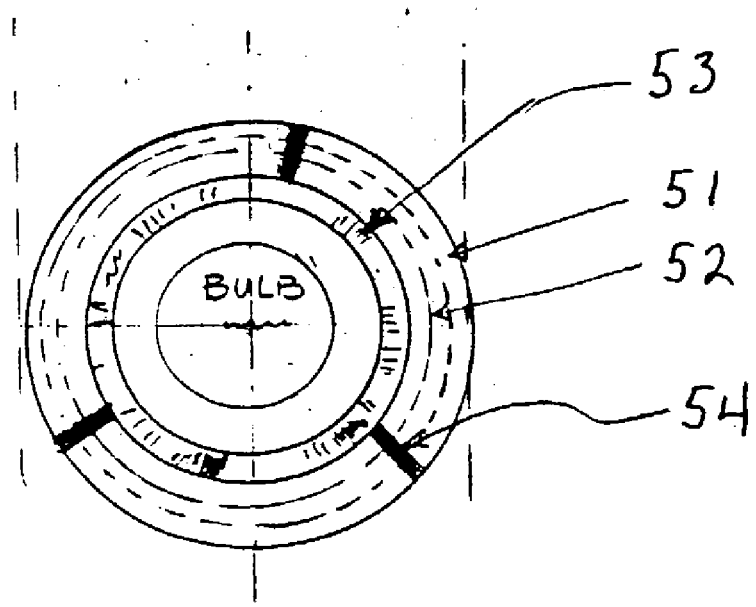

FIGS. 11 and 12 depict an embodiment of light canister that can be used in various preferred embodiments of the current invention. The canisters 36 contain rings of mirrors 51, 52, & 53 that are positioned and angled to capture and redirect the angular light rays into parallel beams 60 before they leave the canister 36 and enter the sauna. This reduces glare and discomfort to the eyes and more closely duplicates the characteristics of sunlight.

FIG. 12 shows the inside of the light canister. The bulb 12 is surrounded by concentric and angled rings of mirrors. There are three sets of concentric mirror rings. Mirror ring one 51 and mirror ring two 52 are mounted to the walls of the canister 36, and mirror ring three 53 is attached to the canister via holding bars 54. Holding bars 54 are painted black and attached to the walls of the canister. In this embodiment, the walls of the canister are also painted black.

After the sauna of the current invention is assembled, it is powered by simply plugging it into a wall socket having standard household current. The user then sets the exterior controls on the control panel 39 for the intensity and duration of the lights, heat, and other amenities such as music, which the user intends to employ. The user can then enter through the door and remain within the sauna any amount of time that the user feels is comfortable and beneficial. The user may use any one feature of the sauna, such as heat, alone or in conjunction with any other feature of the unit. All controlled features have independent controls.

With this phototherapy sauna, the user is in control of the interior environment to his or her own comfort level. Other enjoyable amenities are also possible to add on such as magnetic therapy, tanning lamps, a music system, a video system with an interior screen, aromatherapy, a humidifier, or a fresh air fan. The user could imitate a day at the beach, with a fresh breeze blowing. There are many possibilities for physical and mental enjoyment of the phototherapy sauna. After use of the sauna is completed, the sauna can be disassembled and stored out of the way, or it can be left in its assembled condition.

INDUSTRIAL APPLICABILITY

The invention has applicability to the field of phototherapy and saunas; in particular, this invention describes the only currently available method for delivering combined full body phototherapy and heat benefits in an economic, comfortable and aesthetically pleasing environment. Further, the combined phototherapy and heat benefits may be employed in combination or alone such that the user may enjoy a simple phototherapy session without the added heat, or may employ the heat alone if it is near bedtime and the stimulus of the lights is not desired. The phototherapy sauna of the current invention can be used by individuals or groups of people at a private residence for therapeutic reasons or for recreational or relaxation purposes. The invention disclosed herein can also be used by medical institutions and private health practitioners for medical and therapeutic purposes.

In compliance with the statute, the invention has been described in language more or less specific as to structural features. It is to be understood, however, that the invention is not limited to the specific features shown or described, since the means and construction shown or described comprise preferred forms of putting the invention into effect. Additionally, while this invention is described in terms of being used for providing heat therapy and photo therapy, it will be readily apparent to those skilled in the art that the invention can be adapted to other uses as well. The invention is, therefore, claimed in any of its forms or modifications within the legitimate and valid scope of the appended claims, appropriately interpreted in accordance with the doctrine of equivalents.

What is claimed is:

1. A sauna comprising:
   an enclosure defining a sauna chamber, said sauna chamber having a plurality of interior walls;
   Infrared-heating elements located inside said sauna chamber;
   said infrared heating elements being adjustable for timing and intensity;
   said infrared heating elements being operable off of standard household electric current;
   full spectrum except for ultraviolet lights located within said sauna chamber;
   said full spectrum except for ultraviolet lights being adjustable for timing and intensity, whereby said full spectrum lights can be controlled to gradually increase and decrease in intensity over time for ease of the eyes and to mimic a natural sunrise and sunset;
   and an exterior,
   wherein said full spectrum except for ultraviolet lights are located in canisters at the top of said enclosure and said canisters include a plurality of concentric rings of mirrors that redirect the angled light rays from said full spectrum except for ultraviolet lights into parallel beams before they leave the canister and enter the sauna such that any glare from said lights and discomfort to the eyes of the user is reduced; and the rays coming from said canister more closely duplicates the characteristics of sunlight.

2. The sauna in claim 1 further comprising:
   at least one interior bench to allow comfortable seating;
   an enclosed area under said at least one interior bench such that said enclosed area is sheltered from the heat in said sauna;
   said enclosed area containing electronic equipment for the enjoyment of music or other sound enjoyment;
   a control panel on one of said plurality of interior walls;
   a control panel on said exterior of said sauna; and
   whereby said control panel on said exterior of said sauna and said control panel on said one of said plurality of interior walls can be used to control said infrared heating elements, said full spectrum except for ultraviolet lights, and said electronic equipment.

3. The sauna in claim 1 wherein said sauna is a solid structure;
   said solid structure having a plurality of walls, a ceiling, a floor and a hinged door having a magnetic closure; and
   whereby the interior of said solid structure is said enclosure that defines said sauna chamber.

4. The sauna in claim 3 wherein:
   said solid structure is collapsible for easy shipping and assembly; and
   said walls, said ceiling and said floor contain pre-attached clasp closures and screw fasteners for easy assembly with a minimum of tools.

5. The sauna, in claim 4 wherein;
   said solid, structure is constructed from wood; and
   said walls comprise two layers of wood with an air gap between to allow for sound and heating insulation.

6. The sauna in claim 1 further comprising a sound system, wherein said sound system comprises:
   a plurality of speakers, said speakers being located on at least one of said plurality of interior walls;
   a stereo cassette system with am/fm radio;
   a control panel on one of said plurality of interior walls;
   a control panel on said exterior of said sauna;

whereby said control panel on said exterior of said sauna chamber and said control panel on said one of said plurality of interior walls can be used to control said sound system.

7. The sauna in claim 1 wherein a portion of said full spectrum except for ultraviolet lights are located in a plurality of canisters at the top of said enclosure and the remainder of said full spectrum except for ultraviolet lights in said sauna are located on the interior walls of said sauna.

8. The sauna in claim 1 further comprising a unit for aromatherapy.

9. The sauna in claim 1 further comprising a fan or air circulation system.

10. The sauna in claim 1 wherein at least one of said plurality of interior walls is covered with a light-reflective material, whereby pleasant scenes can be projected onto said light-reflective material.

11. The sauna in claim 1 wherein all controllable elements can be operated independently.

12. The sauna of claim 1 further comprising magnets located within said sauna chamber.

13. A sauna comprising:
a solid structure having a plurality of walls each having an interior surface and an exterior surface, a ceiling, a floor a hinged door having a magnetic closure, and a top, assembled such that said sauna has an interior enclosure and an exterior;
said enclosure being a sauna chamber such that the interior surfaces of said plurality of walls is located within said sauna chamber;
at least one interior bench to allow comfortable seating;
Infrared-heating elements located inside said sauna chamber;
said infrared heating elements being adjustable for timing and intensity;
said top of said sauna being a panel having a plurality of neodymium lights directed into said sauna chamber;
said neodymium lights having the full spectrum of light except for the ultra violet portion of the spectrum and said neodymium lights being adjustable for timing and intensity;
a control panel on one of said plurality of interior wails and a control panel on said exterior of said sauna such that either of said control panels can be used to control said infrared heating elements, and said neodymium lights;
said infrared heating elements being operable off of standard household electric current;
whereby said sauna is constructed from wood, said walls have two layers of wood with an gap between the layers to allow for sound and heating insulation, said sauna is collapsible for easy shipping and configured for ease of assembly; and all controllable elements can be operated independently;
wherein said neodymium lights are located in canisters at the top of said enclosure and said canisters include a plurality of concentric rings of mirrors that redirect the angled light rays from said neodymium lights into parallel beams before they leave the canister and enter the sauna such that any glare from said lights and discomfort to the eyes of the user is reduced; and the rays coming from said canister more closely duplicates the characteristics of sunlight.

14. A method for treating the effects of seasonal affected disorder comprising the steps of:
a) entering a sauna that is solid structure having a plurality of walls each having an interior surface and an exterior surface, a ceiling, a floor a hinged door having a magnetic closure, and a top, assembled such that said sauna has an interior enclosure and an exterior;
said enclosure being a sauna chamber such that the interior surfaces of said plurality of walls is located within said sauna chamber;
said sauna chamber having least one interior bench to allow comfortable seating;
said sauna chamber having infrared heating elements located inside said sauna chamber, said infrared heating elements being adjustable for timing and intensity;
said sauna chamber having a plurality of full spectrum except for ultraviolet lights directed into said sauna chamber, said full spectrum except for ultraviolet lights having the full spectrum of light except for the ultra violet portion of the spectrum and being adjustable for timing and intensity;
wherein said full spectrum except for ultraviolet lights are located in canisters at the top of said enclosure and said canisters include a plurality of concentric lings of mirrors that redirect the angled light rays from said full spectrum except for ultraviolet lights into parallel beams before they leave the canister and enter the sauna such that any glare from said lights and discomfort to the eyes of the user is reduced and the rays coming from said canister more closely duplicates the characteristics of sunlight;
said sauna chamber having a control panel on one of said plurality of interior walls and a control panel on said exterior of said sauna such that either of said control panels can be used to control said infrared heating elements, and said full spectrum except for ultraviolet lights;
said sauna being constructed from wood, said walls having two layers of wood with an gap between the layers to allow for sound and heating insulation, said sauna is collapsible for easy shipping and configured for ease of assembly; all controllable elements in said sauna being independently operable off of standard household electric current;
b) setting the control elements of said sauna to provide the desired light intensity from said full spectrum except for ultraviolet lights and the desired intensity of heat for a desired period of time;
c) activating the light and heat in said sauna; and
d) remaining in said sauna for a desired period of time; and exiting said sauna at the end of said desired period of time.

15. The method of claim 14 wherein said sauna has additional full spectrum except for ultraviolet lights located on the interior walls of said sauna.

16. The method of claim 14 wherein said full spectrum lights are neodymium lights.

* * * * *